(12) United States Patent
Enayati

(10) Patent No.: US 6,527,772 B2
(45) Date of Patent: Mar. 4, 2003

(54) SPLIT RIVET BONE FASTENER

(76) Inventor: Albert Enayati, 809 Carter La., Paramus, NJ (US) 07652

( * ) Notice: Subject to any disclaimer, the term of this patent is extended or adjusted under 35 U.S.C. 154(b) by 158 days.

(21) Appl. No.: 09/737,251

(22) Filed: Dec. 13, 2000

(65) Prior Publication Data

US 2002/0072749 A1 Jun. 13, 2002

(51) Int. Cl.⁷ ............................................. A61B 17/00
(52) U.S. Cl. ......................................... 606/53; 606/60
(58) Field of Search .............................. 606/60, 72, 75, 606/232, 213

(56) References Cited

U.S. PATENT DOCUMENTS 5,882,351 A * 3/1999 Fox .............................. 606/63

* cited by examiner

Primary Examiner—Henry Bennett
Assistant Examiner—Nihir Patel
(74) Attorney, Agent, or Firm—Michael G. Petit

(57) ABSTRACT

Substrates such as soft tissue bone plates are secured to a bone with a reabsorbable or metallic split rivet bone fastener. The split rivet bone fastener consists of two rotatably connected elongate pins: a pivoting pin and a locking pin, rotatably connected to one another by a transverse pivot pin. Each elongate pin comprises a proximal head portion, a distal leg portion and a body portion therebetween. The pivoting pin and the locking pin each have a transverse cylindrical cavity in the body portion thereof which houses the pivot pin. The pivoting pin and the locking pin each have a semicylindrical groove extending from the head portion thereof to the transverse cylindrical cavity which grooves form a cylindrical lumen when juxtaposed. In a preferred embodiment, a substrate fastener such as a suture is affixed to the pivot pin with the two opposing ends of the suture extending proximally through the cylindrical lumen to project outwardly from the head of the fastener. The substrate fastener is used to affix a substrate to the rivet.

6 Claims, 2 Drawing Sheets

SPLIT RIVET BONE FASTENER

BACKGROUND OF THE INVENTION

1. Field of the Invention

The invention discloses a bone fastener device for attaching a substrate such as soft tissue of a bone plate to a bone.

2. Prior Art

Both bioabsorbable and nonbioabsorbable bone fasteners adapted for attaching bone plates and soft tissue, such as, for example tendons and ligaments, to bone are known in the art. Such prior art fasteners include staples and tacks, screws, and rivets. Examples of staple type fasteners are illustrated in U.S. Pat. Nos. 4,454,875 and 4,570,623. Such bone staples generally include barbs on the cross-member which are useful for securely grasping a soft tissue such as a ligament and attaching it to bone.

The second type of fasteners include both screws and screw-washer combinations wherein a hole must be drilled in a bone for the purpose of receiving the screw. Screws may be fabricated from a surgically acceptable, biocompatible metal such as titanium, stainless steel or a cobalt-chromium alloy. Such metallic screws may be self-tapping. In bone fasteners comprising a screw-washer combination, the washer has spikes on one surface operable for grasping tissue, and a central aperture through which the screw is inserted into a bone. If the screw is fabricated from a bioabsorbable material, the hole in the bone must be tapped before the screw can be urged thereinto. Other ligament anchoring systems are disclosed in U.S. Pat. Nos. 4,927,421 and 4,870,957.

The staple and screw types of bone fastening devices possess several disadvantages. For example, staples, which are meant to be hammered into bone, must be made of a strong material, such as a metal. The use of staples is time consuming, traumatic and precludes the use of bioabsorbable polymers as suitable material for staple-type fasteners. As with staples, until such time as stronger and harder bioabsorbable materials become available, self-tapping screws must comprise a biocompatible metal. Both regular and self-tapping screw fasteners require a hole be drilled in the bone prior to use, If the screw comprises a non-metallic bioabsorbable material, the hole must also be tapped in order to receive the screw which requires an additional time consuming step.

In accordance with current art, metallic staples and screw fasteners are either permanently implanted within a bone, or a second surgical operation must be performed in order to remove them. In either case, implantation of metal fasteners does not allow for the gradual transfer of stress back to the bone/soft tissue junction as the healing proceeds. This, in turn, may slow down or impede the healing process. Furthermore, metal screws and staples may migrate from their original site of implantation over a period of time and lodge in a tissue causing pain. Permanently implanted metallic screw and staple fasteners can even migrate from the site of implantation to lodge within a joint, creating significant damage to articulator cartilage and other structures.

To overcome the disadvantages of the screw and staple types of bone fasteners, expandable rivets, both bioabsorbable and metallic, have been developed. Examples of such rivets are disclosed in U.S. Pat. Nos. 5,968,044; 5,911,721; and 5,725,529 to Nicholson et al., and U.S. Pat. No. 5,720,753 to Sander et al. Such rivets, which are either bioabsorbable or metallic, have the advantage that they may be inserted into an untapped hole, thereafter to be expanded, thereby reducing the time required for implantation of the rivets. Prior art rivets include an elongate body portion having an axial bore, an expanded head portion and an expandable leg portion. All of the prior art rivet-type bone fasteners include an expansion pin slidably mounted within the axial bore of the rivet. The bore and a portion of the expansion pin are configured such that movement of the expansion pin in an axial direction forces apart two or more legs on the rivet. The outer surface of the legs is adapted to engage the surrounding bone thereby preventing the rivet from backing out of the hole following implantation. The rivets include means for fastening a substrate to the rivet.

The expansion pins or functionally similar slidable elements used to expand the legs of the rivet bone fasteners, in accordance with the prior art, include a break-away portion which is not implanted in the bone with the rivet. On certain embodiments of the prior art rivets, tension must be applied to the expansion pin in order to expand the legs of the rivet. The tensile strength required to separate the traction portion of the expansion pin from the conical end portion may vary. Such tension may either pull the rivet out of the hole or cause the expansion pin to break prematurely, so that the security of the rivet within the bone is compromised.

Conversely, in other embodiments of the prior art rivets, the expansion pin is advanced into the rivet's axial channel in a distal direction (ie: deeper into the hole) to expand the legs. The expansion pin is urged into the axial channel by means of an insertion tool that is affixed to the expansion pin by frangible means. In the event that the insertion tool prematurely breaks away from the expansion pin, the rivet may not be securely anchored within the hole and prove difficult to remove. Accordingly, there remains a need for a fastener for securing tissue to bone which will have a predictable and sufficient initial anchorage strength to permit gradual load sharing to provide full repair and restoration of function of the tissue and bone. There exists a further need for a fastener device which is easily and rapidly attached to tissue and can be reliably anchored into bone which will not pull out of the bone or migrate from its original position following implantation.

SUMMARY

Rivet bone fasteners are provided in accordance with the present invention which are operable for attaching either an autogenous substrate such as tissue, or an exogenous substrate such as a bone plate, to a bone. Embodiments of the rivet bone fasteners are adapted to meet the variety of demands presented by various surgical procedures employed during orthopedic, plastic and reconstructive surgery. The rivet bone fasteners of the present invention include absorbable, nonabsorbable and hybrid embodiments.

It is a first object of the invention to provide a device which may be used to attach a material substrate to a bone.

It is a further object of the invention to provide a bone fastener device which may be anchored securely in an untapped hole drilled in a bone.

It is another object of the invention to provide a bone fastener device meeting the above objectives which may be permanently implanted in a bone and which will remain anchored in bone after implantation.

It is yet a further object of the invention to provide a bone fastener which may be either non-absorbable, partially absorbable or totally absorbed by the body following implantation therein.

It is yet another object of the invention to provide a rivet bone fastener adapted for insertion into a hole in a bone, thereafter to be expanded to provide non-releasable engagement of the rivet with the wall of the hole.

In the prior art, soft tissue and/or reabsorbable and metallic bone plates are fastened to the bone by the use of resorbable or metallic screws or by a expansion rivet having at least two separable parts.

A: Advantages of a Reabsorbable Split Rivet Bone Fastener

A disadvantage of using reabsorbable screws to secure a bone plate or soft tissue to the bone is the necessity of tapping a screw hole for insertion of the screw. Since reabsorbable screws are not self-tapping, the operating surgeon has to tap a screw hole prior to insertion of the screw in the bone. This procedure is time consuming and, depending on the accessibility of a particular operating site, the surgeon may not be able to tap the screw hole in a straight line. The split rivet bone fastener in accordance with the present invention, whether fabricated from reabsorbable or non-reabsorbable material, obviates the need for tapping a screw hole prior to insertion of the fastener.

The features of the invention believed to be novel are set forth with particularity in the appended claims. However the invention itself, both as to organization and method of operation, together with further objects and advantages thereof may be best be understood by reference to the following description taken in conjunction with the accompanying drawings in which:

DESCRIPTION OF THE PREFERRED EMBODIMENTS

A split rivet bone fastener is disclosed that is useful for fastening substrates such as soft tissue and bone plates to a bone. The split rivet bone fastener consists of two rotatably connected elongate pins: a pivoting pin and a locking pin, rotatably connected to one another by a transverse pivot pin. Each elongate pin comprises a proximal head portion, a distal leg portion and a body portion therebetween. The locking pin and the pivoting pin are substantially mirror images of one another. The pivoting pin and the locking pin each have a transverse cylindrical cavity in the body portion thereof which houses the transverse pivot pin. The pivoting pin and the locking pin each have a semicylindrical groove extending through the head portion thereof and terminating at the transverse cylindrical cavity. The grooves form a cylindrical lumen when juxtaposed. In a preferred embodiment, a substrate fastener such as a suture is affixed to the pivot pin with the two opposing ends of the suture extending proximally through the cylindrical lumen to project outwardly from the head of the fastener. The substrate fastener is used to affix a substrate to the rivet.

Figure 1:
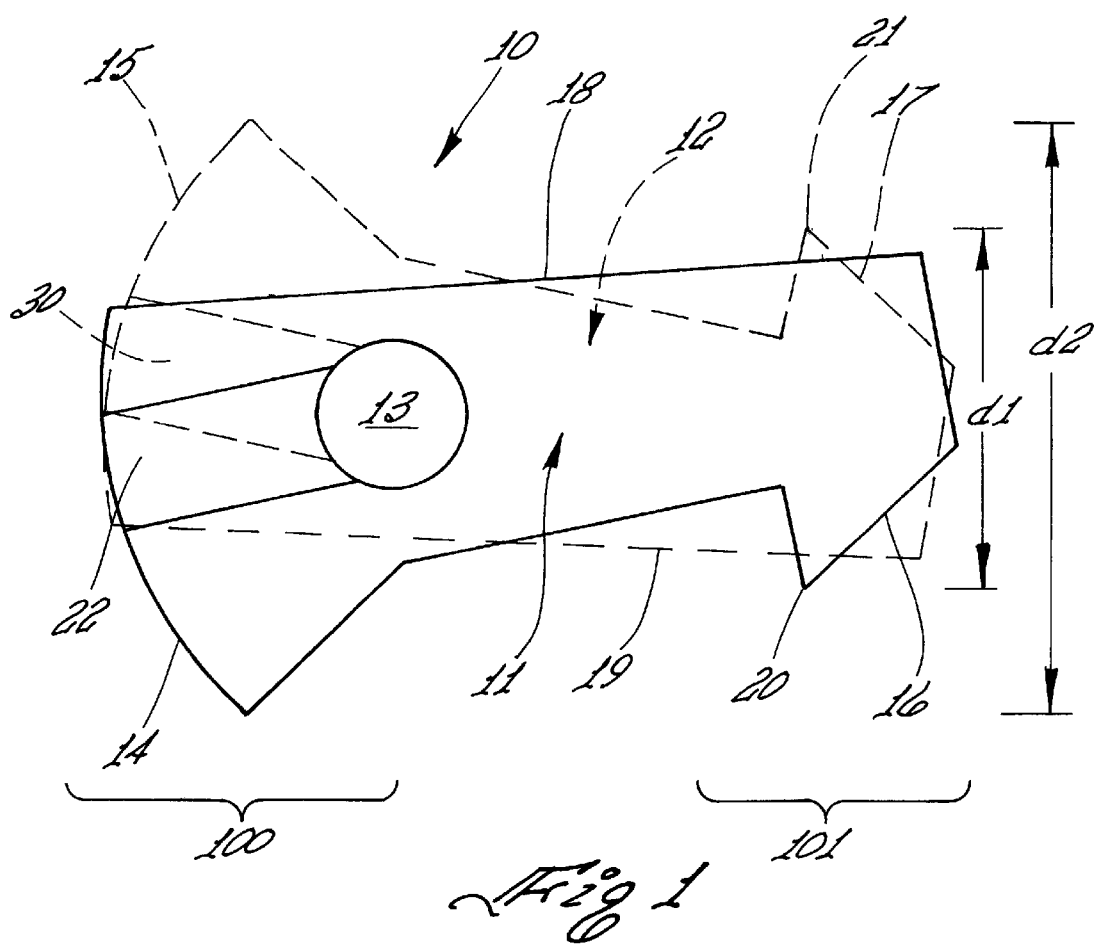
FIG. 1 is a side elevational view of a split rivet bone fastener in accordance with the present invention.

FIG. 1 is a side elevational view of a split rivet bone fastener 10 in accordance with the present invention. The split rivet bone fastener is positioned for insertion into a hole drilled in a bone. A locking pin 11, shown in solid outline in FIG. 1, is rotatably attached to a pivot pin 12 (shown in dashed outline in FIG. 1) by a transverse pivot pin 13. The locking pin 11 and the pivoting pin 12 each have a head portion, 14 and 15 respectively, the head portions 14 and 15 of the respective pins, collectively referred to herein as the expanded head 100 of the split rivet bone fastener. The split rivet 10 further includes a distal portion 101 comprising distal end 16 and distal end 17 of the locking pin 11 and the pivot pin 12 respectively. Each pin 11 and 12 includes a body portion 18 and 19 respectively between the expanded heads and the distal end. When the split rivet 10 is ready to be inserted into a hole drilled in a bone (not shown), the head portion is expanded and has a greatest diameter d1, d1 being greater than the diameter of the hole, and the leg portion has a greatest diameter d2, d2 being less than or equal to the diameter of the hole in the bone. Thus, the distal ends 16 and 17 and body portions 18 and 19 fit snugly within the hole. As the split rivet 10 is further advanced into the hole, the expanded heads 14 and 15 are forced inwardly. As the expanded heads move into alignment, the distal ends 16 and 17 of the locking pin 11 and the pivot pin 12 are forced apart. Barbs 20 and 21 on the distal ends of the locking pin and the pivot pin respectively, engage the bone surrounding the hole, securely holding the split rivet within the hole in locking engagement therewith. When the split rivet is locked into the hole, as described above, grooves 22 and 30 are brought into substantially alignment with one another to form a cylindrical channel.

Figures 2, 2A, 2B:
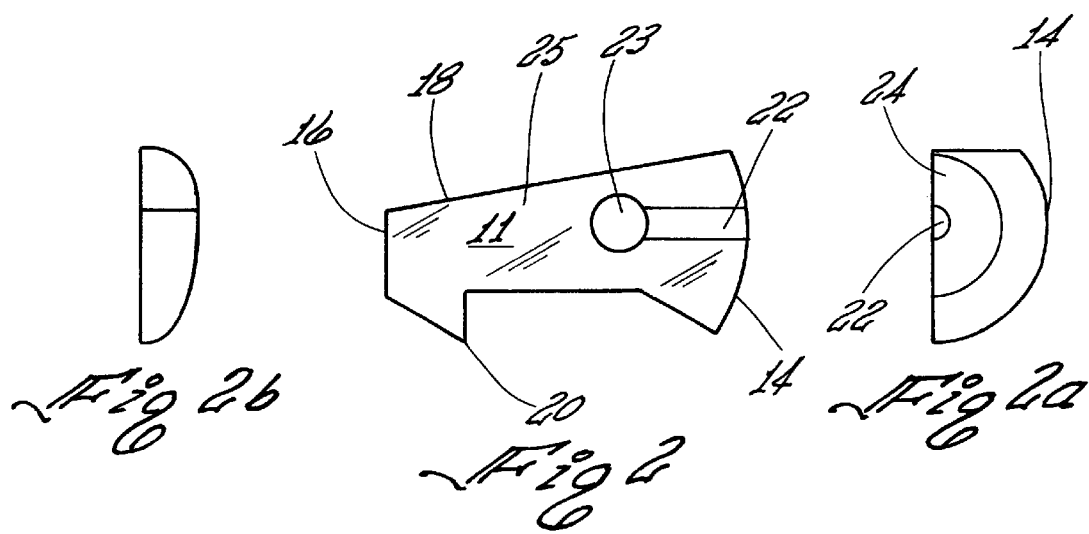
FIG. 2 is a side elevational view of one leg comprising the split rivet bone fastener of FIG. 1.
FIG. 2a is an end view of the leg shown in FIG. 2 viewed from the right.
FIG. 2b is an end view of the leg shown in FIG. 2 viewed from the left.
Figures 3, 3A, 3B:
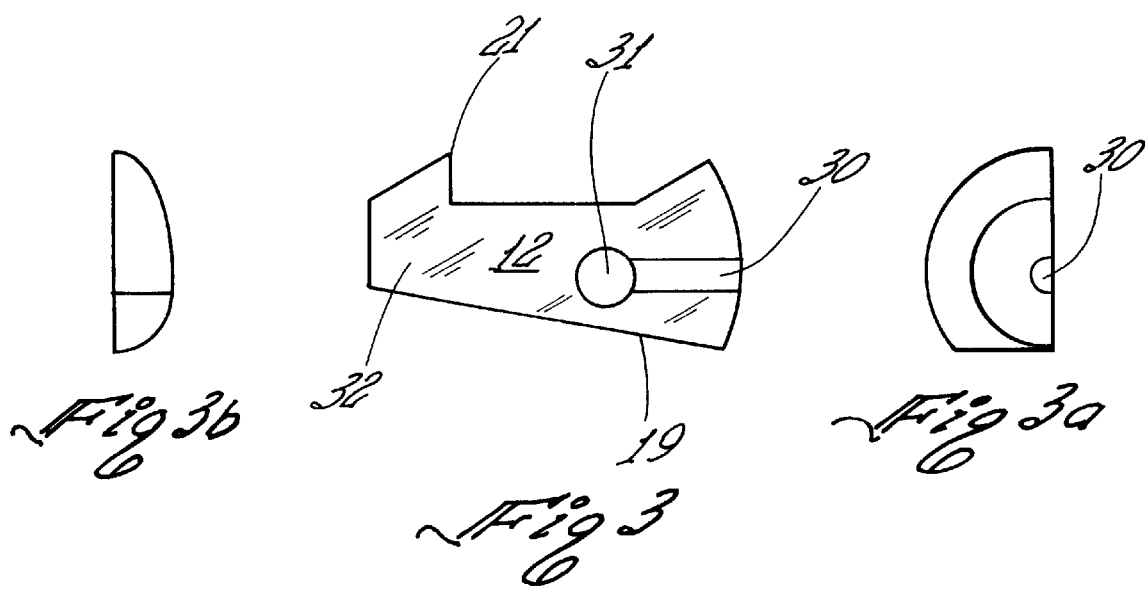
FIG. 3 is a side elevational view of a second leg comprising the split rivet bone fastener of FIG. 1.
FIG. 3a is an end view of the second leg shown in FIG. 3 viewed from the right.
FIG. 3b is an end view of the leg shown in FIG. 3 viewed from the left.
Figure 4:
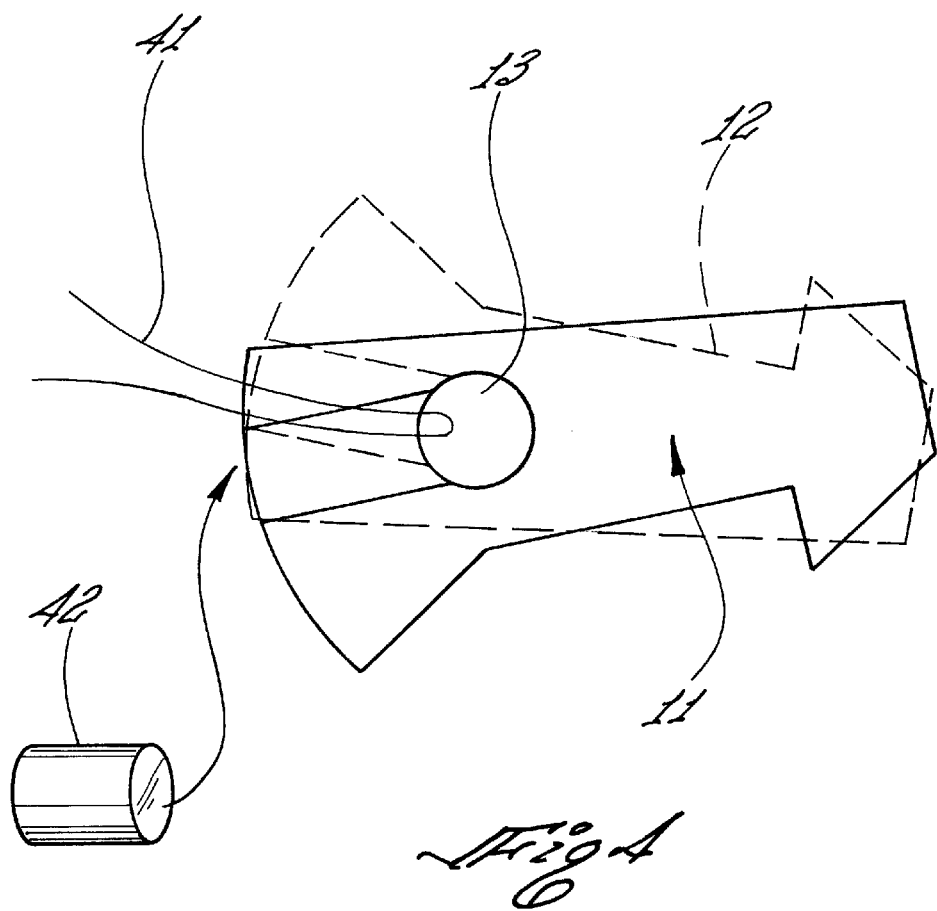
FIG. 4 is a schematic view showing a suture affixed to the locking pin of the split rivet bone fastener.

Turning now to FIG. 2, the locking pin 11 is illustrated in elevational view. A groove 22, which is preferably semicircular in cross-section, extends through the expanded head 14 to a transverse cylindrical cavity 23. The locking pin 11 has an inner facing surface 25. FIG. 2a is a right end view of locking pin 11 showing the expanded head of the locking pin. FIG. 2b is an end-on view of the locking pin 11 viewed from the left. FIG. 3 shows the pivot pin 12 in elevational view. The pivot pin 12 includes a second groove 30, which is preferably semicircular in cross-section. Groove 30 extends along the inner facing surface 32 of the expanded head 14 to a second transverse cavity 31. FIG. 3a is a right end view of pivot pin 12 showing the expanded head of the locking pin. FIG. 3b is a end on view of the pivot pin 12 viewed from the left FIG. 4 illustrate a suture substrate fastener 40 extending proximally from the expanded head portion of the split rivet bone fastener 10. The split rivet bone fastener is assembled by connecting the locking pin and the pivot pin together by means of the transverse pivot pin 13. The transverse pivot pin may advantageously be molded on either the locking pin or the pivot pin with an end projecting from the inner facing surface of the pin and disposed and dimensioned to rotatably engage the transverse cylindrical cavity in the other pin.

In use, the distal ends 16 and 17 of the locking pin 11 and pivot pin 12 are inserted into a pre-drilled hole in a bone, either directly into the bone or through a hole in a bone plate. The hole in the bone has a smaller diameter than the diameter d1 (FIG. 1) of the expanded head portion 100 of the rivet bone fastener 10. As the rivet is further urged to advance into the hole, the two head portions 14 and 15 will be forced together to form a substantially circular head. As the heads are forced together, the leg portions of the locking and pivoting pins (ie: the portion of the pins distal to the pivot pin) will expand. This action will expand the leg into the bone. A cylindrical locking pin (not shown) may be inserted into the cylindrical lumen formed by the alignment of grooves 22 and 30 which it will lock the expanded barbs 20 and 21 in a permanently expanded position.

With reference to FIG. 4, in order to attach a substrate such as soft tissue or a bone plate to the split rivet bone fastener, and hence to the bone, anchoring means is required. Anchoring means includes any means that is operable for attaching a substrate to the split rivet. Most preferably, a suture 41 may be attached to the pivot pin 12, or the transverse pivot pin 13, to extend therefrom through the cylindrical lumen in the head portion 100 of the expanded split rivet. The suture in the cylindrical lumen may also be used as a locking pin to lock the expanded legs in a permanently expanded position within the pre-drilled hole. More preferably, a cylindrical plug or locking pin 42 may be inserted into the lumen formed by alignment of the grooves 22 and 30 when the split rivet 10 is expanded in order to lock the barbs into the bone. The split rivet bone fastener may be conveniently placed within a hole and expanded by means of a suitable insertion instrument (not shown).

In summary, the split rivet bone fastener of the present invention is adapted to be inserted into a hole drilled in a bone, thereafter to be lockingly engaged with the bone. The split rivet includes a locking pin and a pivot pin rotatably connected to one another by means of a transverse pivot pin. The locking pin and the pivot pin include a distal portion having a barb thereon and an expanded head portion. The diameter of the drilled hole is less than the greatest diameter of the legs when the legs are juxtaposed and the head expanded. When the split rivet is advanced into the hole, the expanded head portion is forced to contract. As the expanded head contracts, the halves 14 and 15 comprising the rivet's expanded head portion 100 rotate inwardly toward one another thereby forcing the barbs 20 and 21 to expand. As the barbs expand, the barbs dig into the bone to form a locking relationship with the bone. The locking pin is preferably substantially a mirror image of the pivot pin. The transverse pivot pin 13, used to rotatably attach the locking pin to the pivot pin, maintains the facing relationship between respective inner facing surfaces 25 and 32 of the locking pin 11 and pivot pin 12 during insertion of the split rivet into the hole and during advancement of the split rivet thereinto. A suture is preferably affixed to the locking pin and extends through a groove in the expanded head to provide means for anchoring tissue to the split rivet. The split rivet bone fastener is most preferably fabricated from a bioabsorbable material. A cylindrical locking pin 42, dimensioned to fit within grooves 22 and 30 when the grooves are aligned by expansion of the split rivet, is preferably inserted into the lumen formed by the aligned grooves thereby locking the barbs 20 and 21 of the split rivet bone fastener in locking engagement with the bone and acchoring the split rivet within the hole.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What I claim is:

1. A split rivet bone fastener adapted to be inserted into a hole drilled in a bone, thereafter to be advanced into the hole to form a locking relationship with the bone, the split rivet bone fastener comprising:

(a) an elongate locking pin having a proximal end with an expanded head thereon, and a distal end having a barb thereon, said barb being operable for engaging a wall of a hole drilled in a bone when said distal end of said locking pin is inserted into said hole, said locking pin having a substantially semicircular cross-section and a substantially flat inner facing surface, (b) An elongate pivot pin having a proximal end with an expanded head thereon, and a distal end having a barb thereon, said pivot pin having a substantially semicircular cross-section, and a substantially flat inner-facing surface, said pivot pin being substantially a mirror image of said locking pin, (c) a transverse pivot pin rotatably attaching said locking pin to said pivot pin with said inner facing surface of said locking pin in contact with said inner facing surface of said pivot pin.

2. The split rivet bone fastenet of claim 1 wherein said split rivet is fabricated from a bioabsorbable material.

3. The split rivet bone fastener of claim 1 further comprising a suture affixed to said transverse pivot pin.

4. The split rivet bone fastener of claim 2 further comprising a suture affixed to said transverse pivot pin.

5. The split rivet bone fastener of claim 1 further comprising a groove in said inner facing surface of said locking pin wherein said groove is coextensive with a length of said expanded head portion and extends to said transverse pivot pin.

6. The split rivet bone fastener of claim 5 further comprising a cylindrical locking pin inserted into a cylindrical lumen formed by the alignment of said grooves in said split rivet bone fastener, said cylindrical locking pin being operable for locking said barbs in a permanently expanded position.

* * * * *